US012396812B2

(12) United States Patent
Panescu et al.

(10) Patent No.: US 12,396,812 B2
(45) Date of Patent: Aug. 26, 2025

(54) SYSTEMS AND METHODS FOR ROBOTIC MEDICAL SYSTEM INTEGRATION WITH EXTERNAL IMAGING

(71) Applicant: INTUITIVE SURGICAL OPERATIONS, INC., Sunnyvale, CA (US)

(72) Inventors: Dorin Panescu, San Jose, CA (US); Prashant Chopra, Foster City, CA (US); Jonathan M. Sorger, Belmont, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/306,908

(22) Filed: Apr. 25, 2023

(65) Prior Publication Data

US 2023/0372039 A1   Nov. 23, 2023

Related U.S. Application Data

(63) Continuation of application No. 17/075,163, filed on Oct. 20, 2020, now Pat. No. 11,666,397, which is a
(Continued)

(51) Int. Cl.
*A61B 34/00* (2016.01)
*A61B 17/00* (2006.01)
(Continued)

(52) U.S. Cl.
CPC ........ *A61B 34/32* (2016.02); *A61B 17/00234* (2013.01); *A61B 17/3478* (2013.01);
(Continued)

(58) Field of Classification Search
CPC .......... A61B 17/00234; A61B 17/3478; A61B 2034/105; A61B 2034/107;
(Continued)

(56) References Cited

U.S. PATENT DOCUMENTS

| 6,380,732 | B1 | 4/2002 | Gilboa |
| 6,389,187 | B1 | 5/2002 | Greenaway et al. |

(Continued)

FOREIGN PATENT DOCUMENTS

| CN | 1582863 A | 2/2005 |
| CN | 1612711 A | 5/2005 |

(Continued)

OTHER PUBLICATIONS

Extended European Search Report for Application No. 14798321.7, mailed on Mar. 4, 2017, 13 pages.
(Continued)

*Primary Examiner* — Mark D Remaly
(74) *Attorney, Agent, or Firm* — Haynes & Boone, LLP

(57) ABSTRACT

A medical robotic system and method of operating such comprises taking intraoperative external image data of a patient anatomy, and using that image data to generate a modeling adjustment for a control system of the medical robotic system (e.g., updating anatomic model and/or refining instrument registration), and/or adjust a procedure control aspect (e.g., regulating substance or therapy delivery, improving targeting, and/or tracking performance).

20 Claims, 10 Drawing Sheets

Related U.S. Application Data continuation of application No. 15/428,273, filed on Feb. 9, 2017, now Pat. No. 10,842,575, which is a continuation of application No. 14/278,812, filed on May 15, 2014, now Pat. No. 9,592,095.

(60) Provisional application No. 61/824,298, filed on May 16, 2013.

(51) Int. Cl.
*A61B 17/34* (2006.01)
*A61B 34/10* (2016.01)
*A61B 34/30* (2016.01)
*A61B 34/32* (2016.01)
*A61N 5/10* (2006.01)
*A61B 34/20* (2016.01)

(52) U.S. Cl.
CPC .............. *A61B 34/10* (2016.02); *A61B 34/30* (2016.02); *A61N 5/1077* (2013.01); *A61B 2034/105* (2016.02); *A61B 2034/107* (2016.02); *A61B 2034/2065* (2016.02); *A61B 2034/302* (2016.02); *A61B 2034/306* (2016.02)

(58) Field of Classification Search
CPC ...... A61B 2034/2065; A61B 2034/302; A61B 2034/306; A61B 34/10; A61B 34/30; A61B 34/32; A61N 5/1077
See application file for complete search history.

(56) References Cited

U.S. PATENT DOCUMENTS

| | | | |
|---|---|---|---|
| 7,720,322 | B2 | 5/2010 | Prisco et al. |
| 7,930,065 | B2 | 4/2011 | Larkin et al. |
| 8,010,177 | B2 | 8/2011 | Csavoy et al. |
| 8,112,292 | B2 | 2/2012 | Simon |
| 9,592,095 | B2 | 3/2017 | Panescu et al. |
| 10,842,575 | B2 | 11/2020 | Panescu et al. |
| 11,666,397 | B2 | 6/2023 | Panescu et al. |
| 12,097,000 | B2 | 9/2024 | Panescu et al. |
| 12,161,434 | B2 | 12/2024 | Panescu et al. |
| 12,232,835 | B2 | 2/2025 | Panescu et al. |
| 2006/0013523 | A1 | 1/2006 | Childlers et al. |
| 2006/0281971 | A1 | 12/2006 | Sauer et al. |
| 2007/0055128 | A1 | 3/2007 | Glossop et al. |
| 2007/0167700 | A1 | 7/2007 | Rahn et al. |
| 2007/0293721 | A1 | 12/2007 | Gilboa |
| 2008/0262342 | A1 | 10/2008 | Averbruch |
| 2009/0080737 | A1 | 3/2009 | Battle et al. |
| 2009/0306581 | A1 | 12/2009 | Claus |
| 2010/0082041 | A1 | 4/2010 | Prisco |
| 2010/0217117 | A1 | 8/2010 | Glossop et al. |
| 2010/0292570 | A1 | 11/2010 | Tsukagoshi |
| 2010/0296723 | A1 | 11/2010 | Greer et al. |
| 2011/0202069 | A1 | 8/2011 | Prisco et al. |
| 2012/0065481 | A1 | 3/2012 | Hunter et al. |
| 2012/0116416 | A1 | 5/2012 | Neff et al. |
| 2012/0165652 | A1* | 6/2012 | Dempsey .............. A61N 5/1045 600/410 |
| 2012/0226145 | A1 | 9/2012 | Chang et al. |
| 2012/0239000 | A1 | 9/2012 | Han et al. |
| 2012/0289777 | A1 | 11/2012 | Chopra et al. |
| 2013/0030408 | A1 | 1/2013 | Piferi et al. |
| 2013/0096377 | A1 | 4/2013 | Duindam et al. |
| 2013/0096385 | A1 | 4/2013 | Fenech et al. |
| 2013/0096497 | A1 | 4/2013 | Duindam et al. |
| 2013/0096572 | A1 | 4/2013 | Donhowe et al. |
| 2013/0296883 | A1 | 11/2013 | Anvari |
| 2013/0303890 | A1 | 11/2013 | Duindam et al. |
| 2013/0303891 | A1 | 11/2013 | Chopra |
| 2013/0303893 | A1 | 11/2013 | Duindam et al. |
| 2014/0227804 | A1 | 8/2014 | Hsu et al. |
| 2014/0276002 | A1* | 9/2014 | West ....................... G06T 19/00 600/424 |
| 2014/0369584 | A1 | 12/2014 | Fan et al. |
| 2016/0000302 | A1 | 1/2016 | Brown et al. |
| 2021/0030494 | A1 | 2/2021 | Panescu et al. |
| 2024/0245475 | A1 | 7/2024 | Panescu et al. |

FOREIGN PATENT DOCUMENTS

| | | |
|---|---|---|
| CN | 1806771 A | 7/2006 |
| CN | 101522134 A | 9/2009 |
| CN | 102470013 A | 5/2012 |
| EP | 1849566 A2 | 10/2007 |
| EP | 2277441 A1 | 1/2011 |
| JP | 2004523295 A | 8/2004 |
| JP | 2005529630 A | 10/2005 |
| JP | 2006149560 A | 6/2006 |
| JP | 2007526036 A | 9/2007 |
| JP | 2008018172 A | 1/2008 |
| JP | 2010506600 A | 3/2010 |
| JP | 2012183308 A | 9/2012 |
| WO | WO-0162173 A2 | 8/2001 |
| WO | WO-03041057 A2 | 5/2003 |
| WO | WO-2005013841 A1 | 2/2005 |
| WO | WO-2005043319 A2 | 5/2005 |
| WO | WO-2005081842 A2 | 9/2005 |
| WO | WO-2006124388 A1 | 11/2006 |
| WO | WO-2007027962 A2 | 3/2007 |
| WO | WO-2007141784 A2 | 12/2007 |
| WO | WO-2010078016 A1 | 7/2010 |
| WO | WO-2010093153 A2 | 8/2010 |
| WO | WO-2012052929 A2 | 4/2012 |
| WO | WO-2012085511 A1 | 6/2012 |
| WO | WO-2012088321 A1 | 6/2012 |
| WO | WO-2012114224 A1 | 8/2012 |
| WO | WO-2012172474 A1 | 12/2012 |
| WO | WO-2013050903 A1 | 4/2013 |

OTHER PUBLICATIONS

Extended European Search Report for Application No. EP20175915.6 mailed on Aug. 31, 2020, 8 pages.
International Search Report and Written Opinion for Application No. PCT/US14/038411, mailed on Oct. 16, 2014, 17 pages.
Office Action mailed Jun. 2, 2017 for Chinese Application No. 201480027424.5 filed May 13, 2014, 22 pages.
Partial Supplementary European Search Report for Application No. 14798321.7, mailed on Dec. 21, 2016, 8 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ROBOTIC MEDICAL SYSTEM INTEGRATION WITH EXTERNAL IMAGING

CROSS-REFERENCE TO RELATED APPLICATIONS

This application is a continuation of U.S. patent application Ser. No. 17/075,163, filed Oct. 20, 2020, which is a continuation application of U.S. patent application Ser. No. 15/428,273 (now U.S. Pat. No. 10,842,575), filed Feb. 9, 2017, which is a continuation application of U.S. patent application Ser. No. 14/278,812 (now U.S. Pat. No. 9,592,095), filed May 15, 2014, and entitled "Systems and Methods for Robotic Medical System Integration with External Imaging," which claims the benefit of U.S. Provisional Application No. 61/824,298, filed May 16, 2013, all of which are incorporated by reference herein in their entirety. This patent document is also related to and incorporates by reference the following co-owned applications, all filed on Oct. 14, 2011: U.S. patent application Ser. No. 13/274,208, entitled "Catheter with Removable Vision Probe", U.S. patent application Ser. No. 13/274,198, entitled "Catheters with Control Modes for Interchangeable Probes"; U.S. patent application Ser. No. 13/274,229, entitled "Vision Probe and Catheter Systems"; and U.S. patent application Ser. No. 13/274,237, entitled "Catheter Sensor Systems."

FIELD

The present disclosure is directed to systems and methods for tracking a medical device within a patient anatomy during a medical procedure, and more particularly to systems and methods for efficiently integrating external imaging with a robotic surgical system.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of shape sensors to more accurately describe the shape, pose, and location of the surgical instrument in real space or with respect to pre-procedural or concurrent images. In a dynamic anatomical system and/or in an anatomical region dense with many anatomical passageways, accurately registering the minimally invasive instrument to the anatomical system is a time consuming and processing intensive task. Improved systems and methods are needed for increasing the accuracy and efficiency of systems and methods of registering minimally invasive instruments to the anatomical system.

SUMMARY

By correlating imaging data from an external imaging system with intraoperative surgical system data, more accurate registration and/or control of the surgical system with respect to actual patient anatomy can be achieved.

A medical system can include a robotically-controllable medical instrument(s) that includes a sensor system (e.g., position sensors, shape sensors, etc.) for providing intraoperative information about the pose of the instrument(s) and/or anatomy. As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Concurrently with the positioning of the medical instrument(s) in the patient, an external imaging system (e.g., computed tomography (CT) scanner, positron emission tomography (PET) scanner, fluoroscopic scanner (e.g., C-arm, O-arm), magnetic resonance imaging (MRI) scanner, cone-beam CT scanner, and/or ultrasound system, among others) provides an intraoperative image of the anatomy in which the surgical instrument(s) is located. In some embodiments, the external imaging system can also be mounted on an articulating (e.g., robotically controllable) support structure to provide for greater range of imaging orientations.

A medical robotic system and method for operating the system can involve receiving intraoperative external image data for at least a portion of a patient anatomy, and at least semi-automatically (i.e., at least partially without manual user intervention) controlling the medical robotic system based on the intraoperative external image data (optionally taken from a predetermined region about a treatment target location or relevant portion of the medical robotic system instrument such as a distal tip or tool section).

The system control can, using data extracted from the external image data, then involve at least semi-automatically regulating delivery of a substance (e.g., a therapeutic, analgesic, implant, or marker, among others) to a target location, applying a treatment modality (e.g., ablation, radiation, ultrasound, or electrophoresis, among others) to a target location, adjusting instrument pose at the target location, adjusting a focal therapy parameter (e.g., radiation beam focal point or cross section, among others), and/or tracking the interaction of the instrument with the tissue at the target location.

A medical robotic system and method for the system can involve receiving intraoperative external image data for at least a portion of a patient anatomy, and at least semi-automatically applying a modeling adjustment to the control system for the medical robotic system based on the intraoperative external image data (optionally taken from a predetermined region about a treatment target location or relevant portion of the medical robotic system instrument such as a distal tip or tool section).

The modeling adjustment can, using data extracted from the external image data, involve automatically or semi-automatically updating the anatomical model of the patient anatomy used for intraoperative navigation based on the intraoperative external image data (e.g., by extracting anatomic feature and/or instrument pose data from the intraoperative external image data using image processing techniques), and/or refining the registration between the patient, instrument, and/or anatomic model (e.g., by extracting data corresponding to fiducial elements such as artificial markers or known anatomic landmarks/structures from the intraoperative external image data to establish common reference frames for the patient, instrument, and/or anatomic model as appropriate.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X,Y,Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1A:
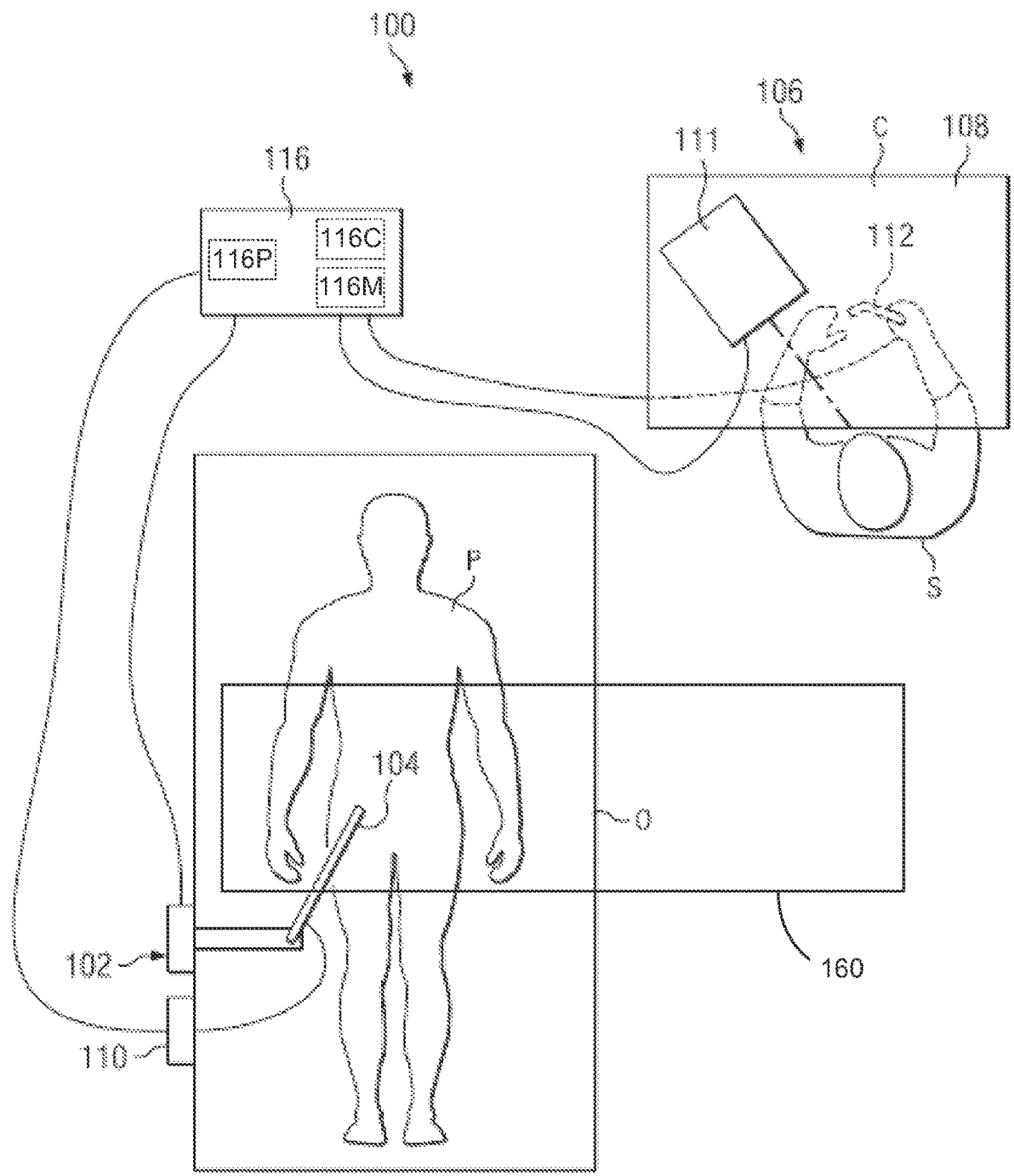
FIG. 1A is a robotic medical system, in accordance with embodiments of the present disclosure.

Referring to FIG. 1A of the drawings, a robotic surgical system is generally indicated by the reference numeral 100. Note that as used herein, "surgical" can refer to any medical procedure performed on a patient, including without limitation operative procedures (e.g., tissue extraction or manipulation), therapeutic procedures (e.g., medicament delivery), and diagnostic procedures (e.g., tissue examination or biopsy). As shown in FIG. 1A, the robotic system 100 generally includes a surgical driver assembly 102 for operating a surgical instrument 104 in performing various procedures on the patient P. The assembly 102 is mounted to or near an operating table O. A master assembly 106 allows the clinician S (e.g., a surgeon or interventionalist) to view the surgical site and to control the driver assembly 102.

In alternative embodiments, the robotic system may include more than one driver assembly. The exact number and configuration of driver assemblies will depend on the surgical procedure and the space constraints within the operating room among other factors.

The master assembly 106 may be located at a clinician's console C which is usually located in the same room as operating table O. However, it should be understood that the clinician S can be located in a different room or a completely different building from the patient P. Master assembly 106 generally includes an optional support 108 and one or more control device(s) 112 for controlling the driver assemblies 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the clinician with telepresence, or the perception that the control device(s) 112 are integral with the instruments 104 so that the clinician has a strong sense of directly controlling instruments 104 (although in other embodiments, the control device(s) 112 may have more or less degrees of freedom than the associated surgical instruments 104). In some embodiments, the control devices 112 are manual input devices which move with six degrees of freedom, and which may also include an actuatable handle for actuating instruments (for example, for closing grasping jaws, applying an electrical potential to an electrode, delivering a medicinal treatment, or the like).

A visualization system 110 may include a viewing scope assembly (described in greater detail below) such that a concurrent or real-time in-situ image of the surgical site (i.e., an image taken at the surgical site) is provided to clinician console C. The concurrent image may be, for example, a two or three dimensional image captured by an endoscope or similar imaging element positioned within the surgical site. In this embodiment, the visualization system 100 can include endoscopic components that may be integrally or removably coupled to the surgical instrument 104. However in alternative embodiments, a separate endoscope, attached to a separate driver assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

A display system 111 may display an image of the surgical site and surgical instruments captured by the visualization system 110. The display system 111 and the master control devices 112 may be oriented such that the relative positions of the imaging device in the scope assembly and the surgical instruments are similar to the relative positions of the clinician's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the surgical instruments 104.

Alternatively or additionally, display system 111 may present images of the surgical site recorded and/or modeled preoperatively and/or intraoperatively by an external imaging system 160 that can use imaging technology such as, computerized tomography (CT), magnetic resonance imaging (MRI), positron emission tomography (PET), fluoroscopy, thermography, ultrasound, optical coherence tomography (OCT), thermal imaging, impedance imaging, laser imaging, or nanotube X-ray imaging, among others. The presented images may include two-dimensional, three-dimensional, or four-dimensional images. Note that as used herein, "external imaging" or "external image" refers to an image of the target anatomy taken from outside the patient, as opposed to "in-situ" images taken from within the patient, regardless of the specific imaging modality (e.g., ultrasound can be used for both external imaging and/or in-situ imaging).

In some embodiments, the display system 111 may alternatively or additionally display a virtual navigational image in which the actual location of the surgical instrument is registered (i.e., dynamically referenced) with preoperative or intraoperative images to present the clinician S with a virtual image of the internal surgical site at the location of the tip of the surgical instrument. An image of the tip of the surgical instrument or other graphical or alphanumeric indicators may be superimposed on the virtual image to assist the clinician controlling the surgical instrument. Alternatively, the surgical instrument may not be visible in the virtual image.

In other embodiments, the display system 111 may alternatively or additionally display a virtual navigational image in which the actual location of the surgical instrument is registered with preoperative or concurrent intraoperative images to present the clinician S with a virtual image of the surgical instrument within the surgical site from an external viewpoint. An image of a portion of the surgical instrument or other graphical or alphanumeric indicators may be superimposed on the virtual image to assist the clinician controlling the surgical instrument.

As shown in FIG. 1A, a control system 116 includes at least one processor 116P and typically a plurality of processors for effecting control between the surgical driver assembly 102, the master assembly 106, and the image and display system 110. The control system 116 also includes software programming instructions to implement some or all of the methods described herein. In various embodiments, such software programming instructions can be stored on non-transitory computer readable media 116C, such as an optical disk(s), a magneto-optical or solid state hard drive(s), flash memory, or any other media type(s). In various embodiments, control system 116 can include one or more computer memories 116M for receiving and/or storing input data, such as model data, sensor data, image data, among others.

While control system 116 is shown as a single block in the simplified schematic of FIG. 1A, the system may comprise a number of data processing circuits (e.g., on the surgical driver assembly 102 and/or on the master assembly 106), with at least a portion of the processing optionally being performed adjacent an input device, a portion being performed adjacent a driver assembly, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instruments 104 to the hand-operated control device 112. Any suitable conventional or specialized servo controller may be used. A servo controller may be separate from, or integral with driver assemblies 102. In some embodiments, the servo controller and driver assembly are provided as part of a robotic arm cart positioned adjacent to the patient's body. The servo controller transmits signals instructing the driver assemblies to move instruments which extend into an internal surgical site within the patient body via openings in the body.

Each of the driver assemblies 102 that support a surgical instrument 104 may comprise one or more articulatable (typically, although not necessarily exclusively, manually articulable) positioning/support linkages, commonly referred to as set-up joints. The driver assemblies 102 may include a series of actuators (e.g., motors). These actuators, which may be integrated with or removably coupled to surgical instrument 104, actively move surgical instrument 104 in response to commands from the control system 116. In particular, the actuators can advance surgical instrument 104 into a naturally or surgically created anatomical orifice and/or to move the distal end of surgical instrument 104 in multiple degrees of freedom that may include three degrees of linear motion (e.g., X,Y,Z linear motion) and three degrees of rotational motion (e.g., roll, pitch, yaw). Additionally or alternatively, the actuators can be used to actuate an articulatable or deployable end effector of instrument 104 (e.g., for grasping tissues in the jaws of a biopsy device or the like).

Figure 1B:
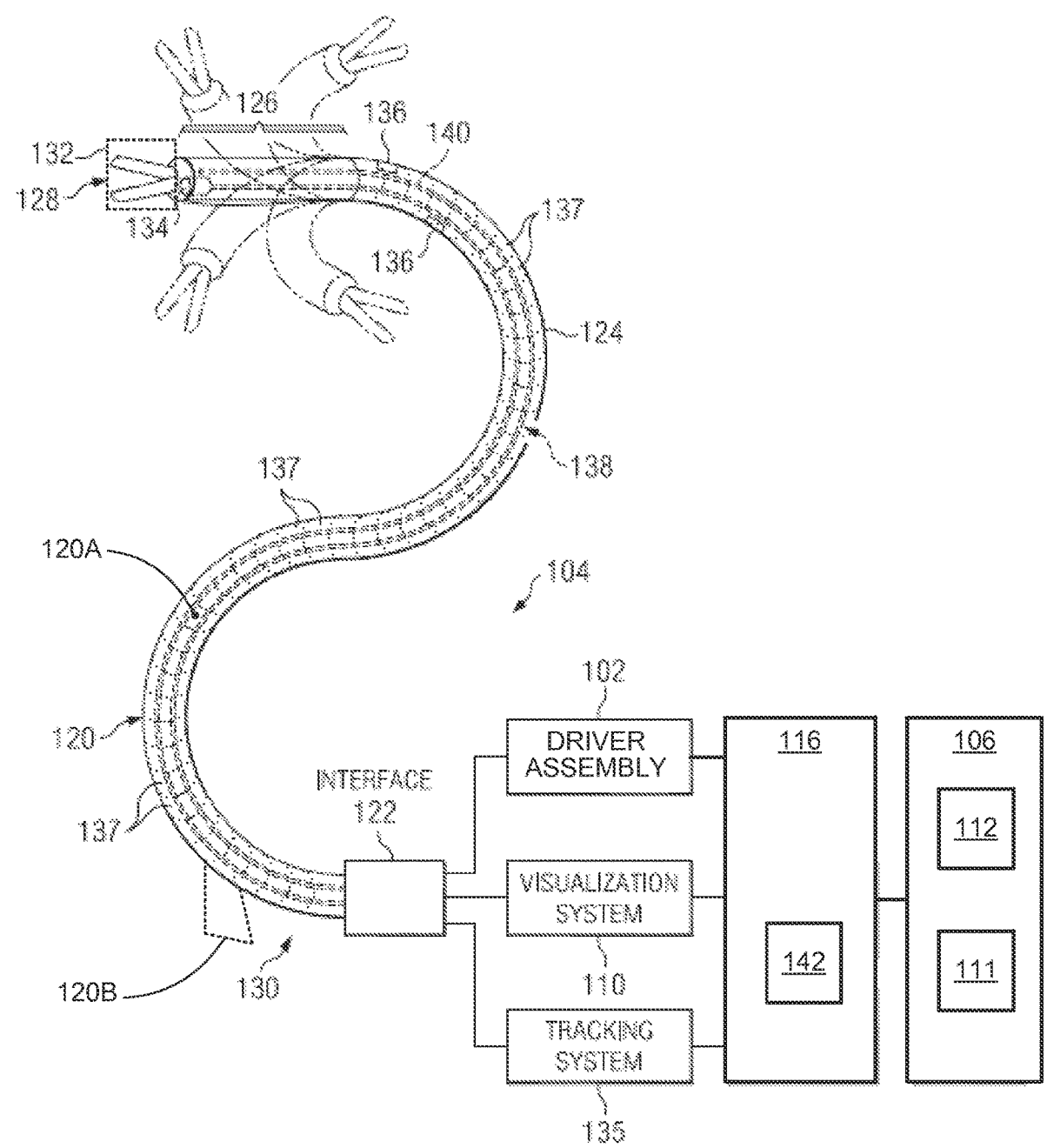
FIG. 1B illustrates a medical instrument system utilizing aspects of the present disclosure.

FIG. 1B illustrates an embodiment of surgical instrument system 104 and its interfacing systems. Surgical instrument system 104 includes a flexible instrument 120 coupled by an interface 122 to driver assembly 102 and visualization system 110. The instrument 120 has a flexible body 124, a tip 126 at its distal end 128, and the interface 122 at its proximal end 130.

In some embodiments, body 124 can be formed from a flexible tube (e.g., a braided structure such as a woven wire tube with inner or outer layers of a flexible or low friction material such as polytetrafluoroethylene (PTFE), a bundle of lumens or tubes held together by a braided jacket and a reflowed (i.e., fused by melting) jacket of a material such as Polyether Block Amide (Pebax), an extrusion of a polymer material such as Pebax, a metal coil, a series of linked elements, a metal tube with cutouts, and/or any other elongate flexible structure), that can, in various embodiments, exhibit a variety of different constructions over its length. In various other embodiments, flexible body can further house, or be integrated with cables, linkages, or other steering controls (not shown) that extend at least partially between the interface 122 and the tip 126 to controllably bend or turn the tip as shown for example by the dotted line versions of the bent tip 126, and in some embodiments control an optional end effector 132.

The flexible instrument may be steerable, including the steering controls previously described, or may be non-steerable with no integrated mechanism for operator control of the instrument bending. Although depicted as a set of jaws for exemplary purposes, optional end effector 132 may be any working distal part that is operable for a medical function, e.g., for effecting a predetermined usage with respect to a target tissue. For instance, some end effectors have a single working member such as a scalpel, a blade, needle, or an electrode. Other end effectors such as shown in the embodiment of FIG. 1B, have a pair or plurality of working members such as forceps, graspers, scissors, staplers, vessel sealers, biopsy tools, suturing tools, or clip appliers, for example. Examples of electrically activated or enabled end effectors include electrosurgical electrodes, ablation elements, transducers, sensors, cameras, probes, and the like. End effectors may also include conduits to convey fluids, gases or solids to perform, for example, suction, insufflation, irrigation, treatments requiring fluid delivery, accessory introduction, biopsy extraction and the like.

In other embodiments, flexible body 124 can define one or more working lumens 120A through which surgical instruments (such as optional end effector 132) can be deployed (e.g., via an optional auxiliary input port 120B) and used at a target surgical location. In various embodiments, such working lumens 120A can be integrated into instrument 120 together with optional end effector 132 and/or other functional elements.

The instrument 120 can also include an image capture element 134 which may include a stereoscopic or monoscopic camera disposed at the distal end 128 for capturing in-situ images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum. In various other embodiments, image capture element 134 can include any type of imaging system, such as a confocal microscope, OCT system, and ultrasonic probe, among others.

In some embodiments, instrument 120 can function as a catheter or guide tube having a working lumen 120A that houses a vision probe that is interchangeable with one or more medical probes or tools. For example, in some embodiments, image capture element 134 can be implemented as a vision probe sized to fit within working lumen 120A, such that the vision probe can be removed and replaced with a medical probe used in a medical procedure. The interchanging of the vision and medical probes may permit the instrument 120 to have a smaller diameter and thus navigate smaller passages than would a similar system that simultaneously accommodates both vision and medical systems. Alternatively, interchanging probes may allow more space for vision and medical systems having greater functionality than might a catheter that must simultaneously accommodate both vision and medical systems.

A tracking system 135 can include a position sensor system 136 (e.g., an electromagnetic (EM) sensor system) and/or a shape sensor system 138 a sensor system for determining the position, orientation, speed, pose, and/or shape of the distal end 128 and optionally one or more segments 137 (regions) along the instrument 120. Although only an exemplary set of segments 137 are depicted in FIG. 1B, the entire length of the instrument 120, between the distal end 128 and the proximal end 130 and including the tip 126 may be effectively divided into segments. The tracking system 135 may be implemented as hardware, firmware, software or a combination thereof which interact with or are otherwise executed by one or more computer processors, which may include the processors of a control system 116.

In some embodiments, position sensor system 136 can be an EM sensor system that includes one or more conductive coils that may be subjected to an externally generated electromagnetic field. Each coil then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an exemplary EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

In some embodiments, shape sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 µm. In other embodiments, the dimensions may be larger or smaller.

The optical fiber 140 forms a fiber optic bend sensor for determining the shape of the instrument 120. In one alternative, optical fibers including Fiber Bragg Gratings (FBGs) are used to provide strain measurements in structures in one or more dimensions. Various systems and methods for monitoring the shape and relative position of a optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as EM sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding 146. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber 140 is used to monitor the shape of at least a portion of the instrument 120. More specifically, light passing through the optical fiber 140 is processed by the tracking system 135 for detecting the shape of the surgical instrument 120 and for utilizing that information to assist in surgical procedures. The tracking system 135 may include a detection system for generating and detecting the light used for determining the shape of the instrument 120. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images and/or the intraoperatively taken images to provide the clinician or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 1B, the instrument 104 can be teleoperated within the robotic surgical system 100. In an alternative embodiment, the driver assembly and associated control system/master assembly may be replaced by direct operator control. In the direct operation alternative, various handles and operator interfaces may be included for handheld operation of the instrument.

Control system 116 controls actuators (e.g., included in drive interface 122, driver assembly 102, control system 116, and/or master assembly 106) to steer distal tip 126. In general, control logic operates in response to commands from a user (e.g., a clinician or other medical personnel using system 100), and optionally in response to sensor signals (e.g., from EM sensor(s) 136 and/or shape sensor system 138). However, as noted above, in some embodiments control system 116 can operate in response to sensor signals—for example to maintain or acquire a previously identified working configuration.

Figure 2A:
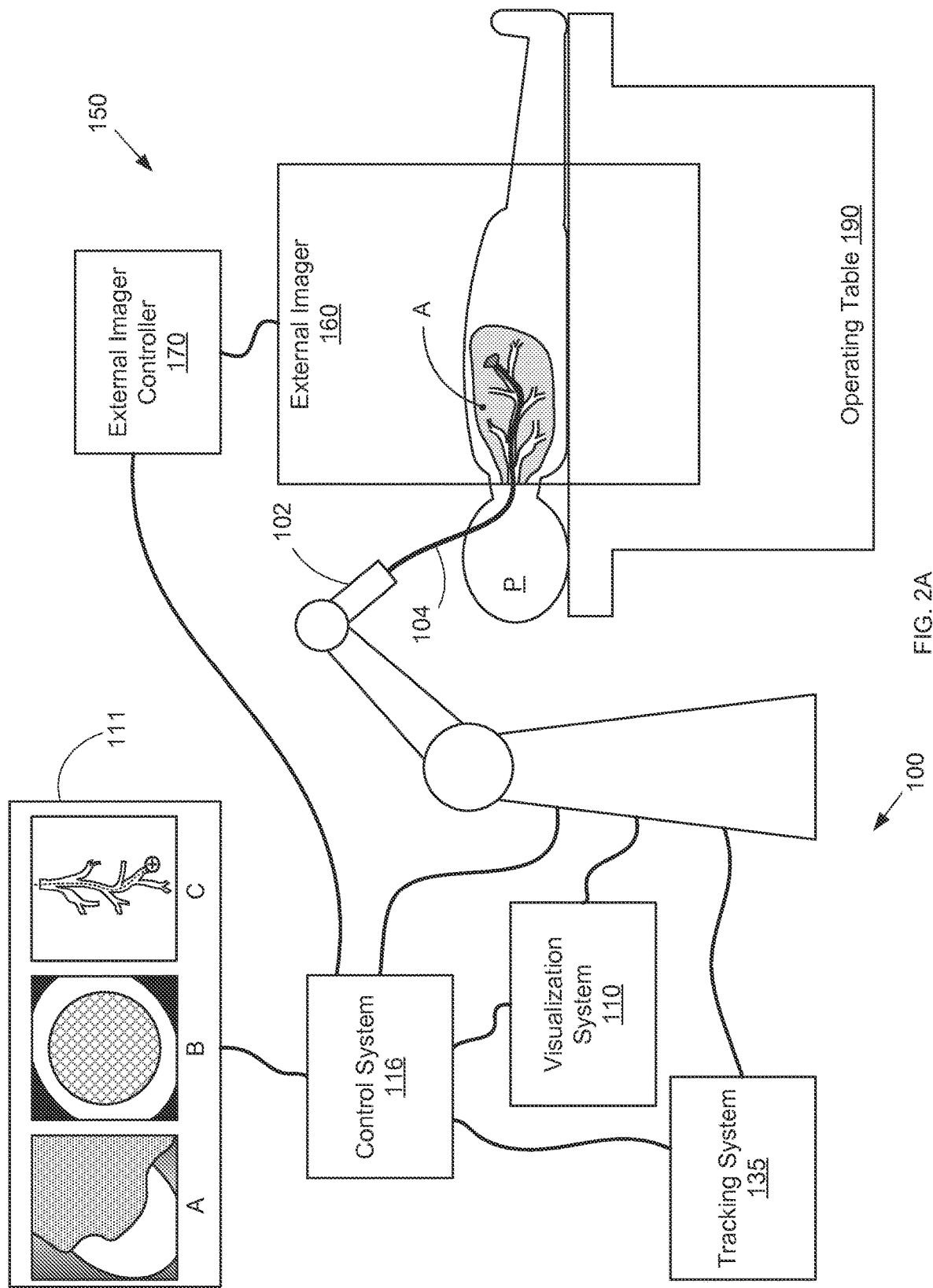
FIG. 2A shows the robotic medical system of FIGS. 1A and/or 1B in conjunction with an external imaging system.

FIG. 2A shows an embodiment of surgical system 100 in which external imaging system 150 is used to enhance the performance of a surgical procedure on patient P. Note that while driver assembly 102 and instrument 104 are depicted and described herein as a "single arm" system with a flexible instrument for exemplary purposes, various other embodiments can include more rigid instrument systems (e.g., the Mako RIO® system) and/or multi-arm robotic systems (e.g., the Intuitive Surgical da Vinci® surgical system), among others. In various other embodiments, driver assembly 102 and instrument 104 can even be an alternative minimally invasive or non-invasive treatment or diagnostic system, such as focal therapy system (e.g., interstitial laser therapy system, focal cryoblation system, high-intensity focused ultrasound (HIFU) system, electroporation system, photodynamic therapy system, and/or external beam radiotherapy system, among others).

As shown in FIG. 2A, driver assembly 102 guides instrument 104 into a target anatomy A of patient P (here depicted as the lungs for exemplary purposes). The behavior of driver assembly 102 and instrument 104 are controlled by control system 116, with sensor data (e.g., position data, shape data, kinematic data, etc.) from instrument 104 (and optionally driver assembly 102) being collected and provided to control system 116 (e.g., by tracking system 135). Similarly, images taken by instrument 104 (e.g., taken via one or more cameras integrated into instrument 104, or positioned on/in instrument 104) can be processed and provided to conrol system 116 by visualization 110. This image data can be presented as a live in-situ image (e.g., image A) on display system 111 (e.g., a computer or video monitor). In various embodiments, virtual in-situ images (e.g., image B) can additionally or alternatively be shown on display system 111, based on the sensor data provided by tracking system 135 and a computer model of anatomy A. In various other embodiments, display system 111 can show any other relevant information, such as a navigational overview of anatomy A (e.g., image C), indicating the pre-planned and/or actual trajectory of instrument 104 in patient P.

Often, a composite image such as image C that combines both instrument and anatomy information taken from different sources (e.g., sensor-based instrument pose information combined with preoperatively or intraoperatively generated anatomical model) is an important element of a minimally invasive surgical procedure. Such a depiction provides a clinician with a visual indication of the overall progress of the procedure that generally cannot be provided by instrument-based imaging equipment (e.g., endoscopic cameras, radial ultrasound probe, etc.) due to the relatively short-range, localized imaging such equipment provides. Compared to such localized imaging, composite image C can show a much more global perspective of an instrument relative to the overall anatomy (or at least relative to a much larger portion of the anatomy). For example, as indicated in image C, in a branching anatomy such as the airway tree in the lungs, composite image C can indicate not only the pose of the distal end region of instrument 104 relative to a target node, but also the path taken by instrument 104, including the specific airway branches traversed by instrument 104. Note that while image C is depicted as a frontal view (i.e., frontal plane of anatomy A) for exemplary purposes, in various other embodiments, image C can be a sagittal view, 3D view, or any other perspective that provides a desired representation of the instrument/anatomy relationship.

Naturally, the accuracy of composite image C relies on an accurate registration between the instrument and the patient anatomy and/or accurate registration between the instrument and the anatomical model. Typically, this registration is based on instrument sensor data (e.g., EM or shape sensors having known relationships reference locations/fiducials attached to the patient anatomy and correlated to reference locations/fiducials in the anatomical model). However, due to the compliance and deformability of patient anatomies, and also due to inherent sensor tolerances, this sensor-based registration can deviate significantly from the actual pose of the instrument relative to the patient anatomy. To mitigate such discrepancies between sensed and actual registration, various algorithmic and/or data analysis approaches can be used, such as described in co-owned, co-pending U.S. patent application Ser. Nos. 13/892,924, 13/893,040, 13/892,871, and 13/893,008, all of which are herein incorporated by reference. Such approaches, while providing accurate registration in many instances, may still be subject to inaccuracies due to anatomical/sensor variations.

Accordingly, in conjunction with the operation (e.g., positioning and/or actuation) of the surgical instrument(s) in the patient, external imaging system 150 (e.g., computed tomography (CT) scanner, positron emission tomography (PET) scanner, fluoroscopic scanner (e.g., C-arm, O-arm), magnetic resonance imaging (MRI) scanner, cone-beam CT scanner, and/or ultrasound system, among others) can be used to provide an intraoperative image (e.g., 2D, 3D, static view, live view, 360° view, wedge view, or any other type of view) of anatomy A and/or instrument 104. In some embodiments, the external imaging system can also be mounted on an articulating (e.g., robotically controllable) support structure to provide for greater range of imaging orientations.

Imaging system 150 includes an external imager 160 (e.g., gantry with x-ray source and receptor) for capturing and generating the external image data, and an external imager controller 170 for processing that data into usable image data (e.g., tomographic reconstruction of the scanned site). In some embodiments, external imager 160 can be mounted on an articulating (e.g., robotically controllable) support structure to provide for greater range of imaging orientations. Control system 116 can then use this image data from external image controller 170 to enhance the procedure being performed on patient P.

In some embodiments, imaging system 150 can work in conjunction with instrument 104 and/or driver assembly 102 to refine and localize the imaging area, for example to increase the imaging resolution for a given exposure time, or to reduce radiation exposure time. For example, in some embodiments, pose data associated with distal tip region 126 of instrument 104 (e.g., a signal directly from a fiducial, tracker, beacon, or other indicator at or near a distal end of instrument 104, or sensor data such as EM sensor, shape sensor, optical sensor data for distal tip region 126) can guide the operation of imaging system 150.

Figure 2B:
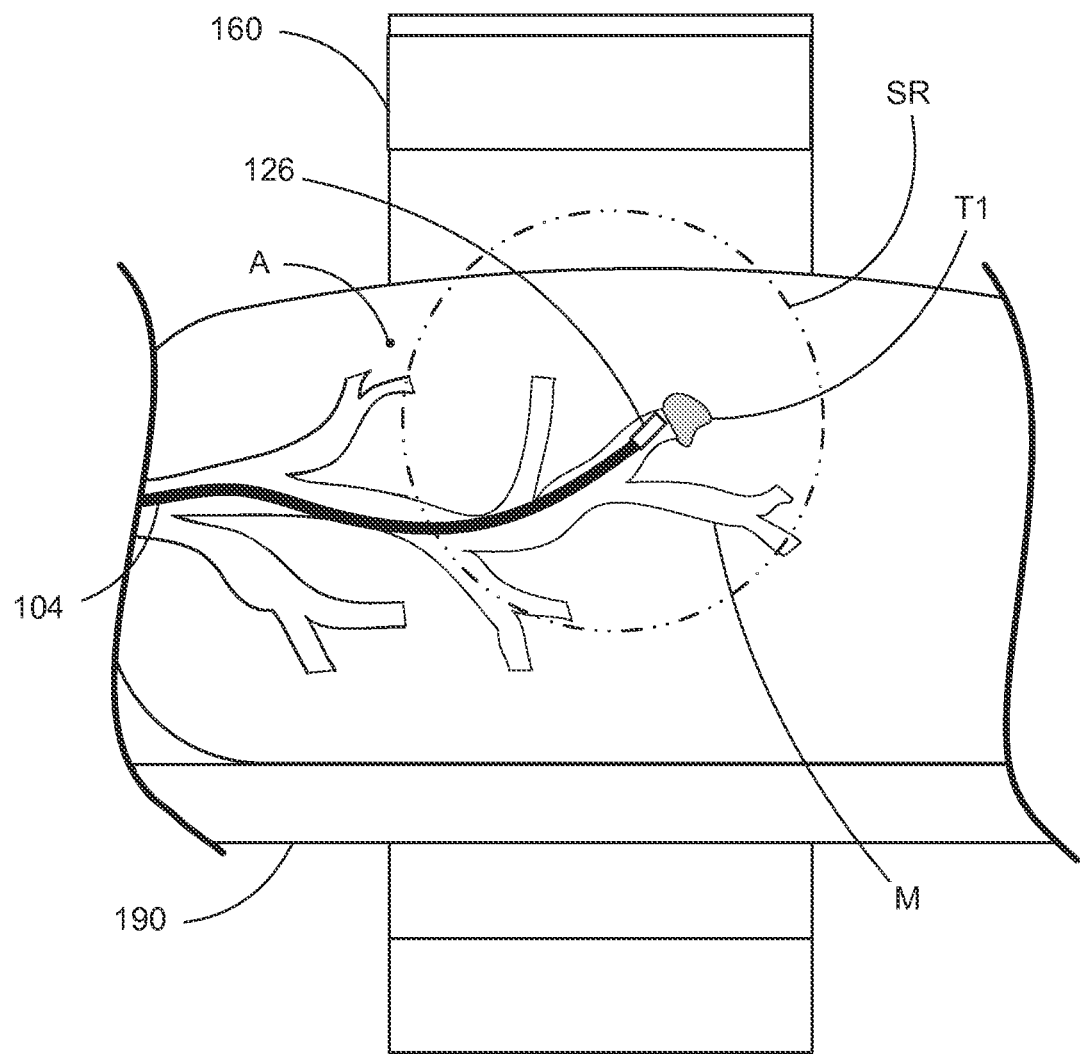
FIGS. 2B-2F shows various operational and control aspects of the robotic medical system of FIG. 2A.
Figure 2C:
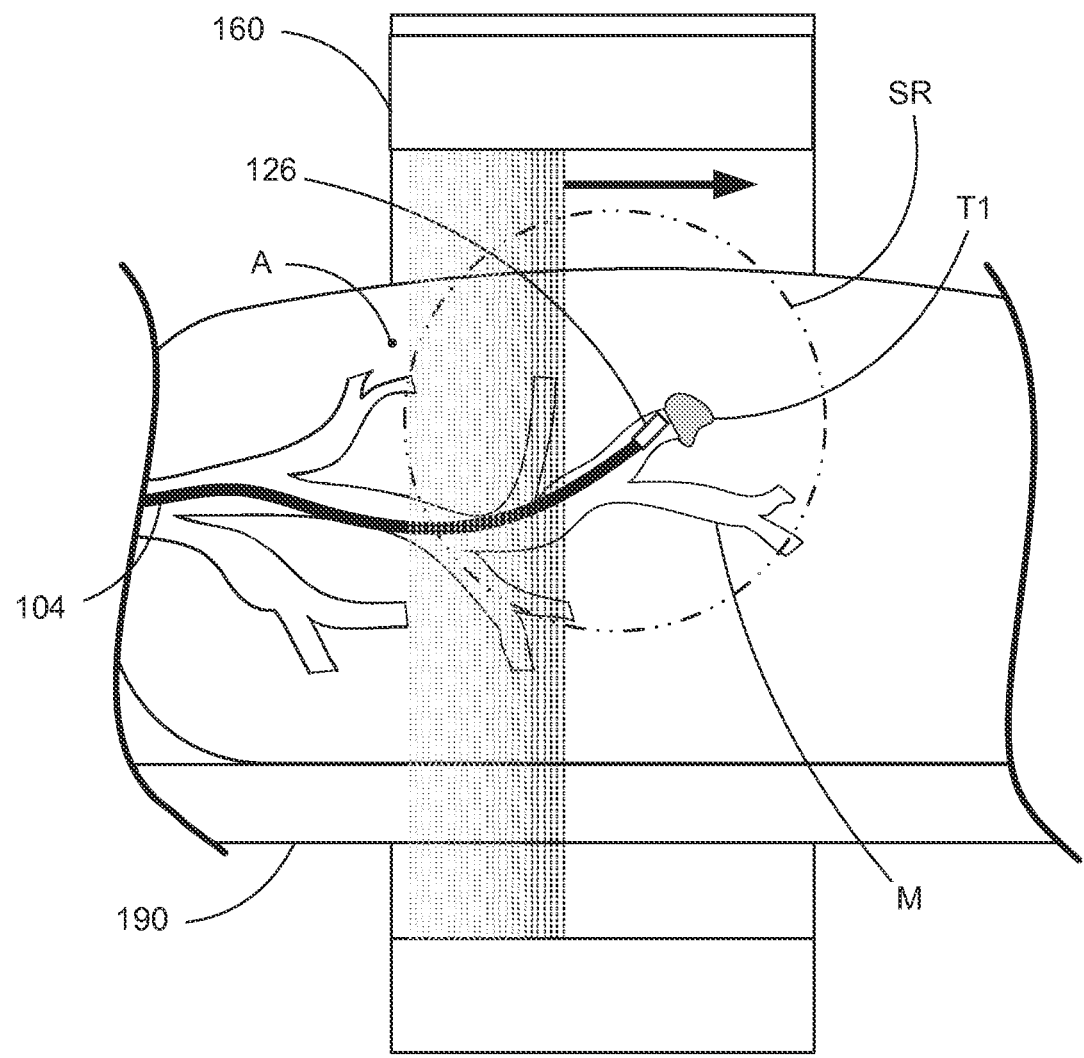

For example, as shown in FIG. 2B, a scan region SR can be defined around tip 126 (e.g., a predetermined, selectable, or user-indicated region around tip 126). External imager 160 can then scan just within around scan region SR (e.g., take CT slices or wedges only within scan region SR) to generate relevant external image data, as shown in FIG. 2C. Note that while scan region SR is depicted as a circular or spherical region for exemplary purposes, in various other embodiments, scan region SR can take any size or shape, and need not be centered around tip 126 (e.g., in some embodiments, scan region SR could extend some distance beyond a distal tip 126 to ensure that the working area of instrument 104 is imaged by external imager 160). In other embodiments, scan region SR could be defined with respect to a target location or feature T1 in anatomy A, such as a nodule, tumor, airway bifurcation, organ, or even a user-identified location in anatomy A.

Regardless of whether localized or general external image data is provided by imaging system 150, that data can then be used by control system 116 to enhance the performance of the procedure on patient P. For example, in some embodiments, the intraoperative external image data from imaging system 150 can be used in conjunction with an existing model of anatomy A (e.g., a preoperatively generated CT model, optionally modified intraoperatively) to provide a more accurate representation of the immediate intraoperative environment.

Figure 2D:
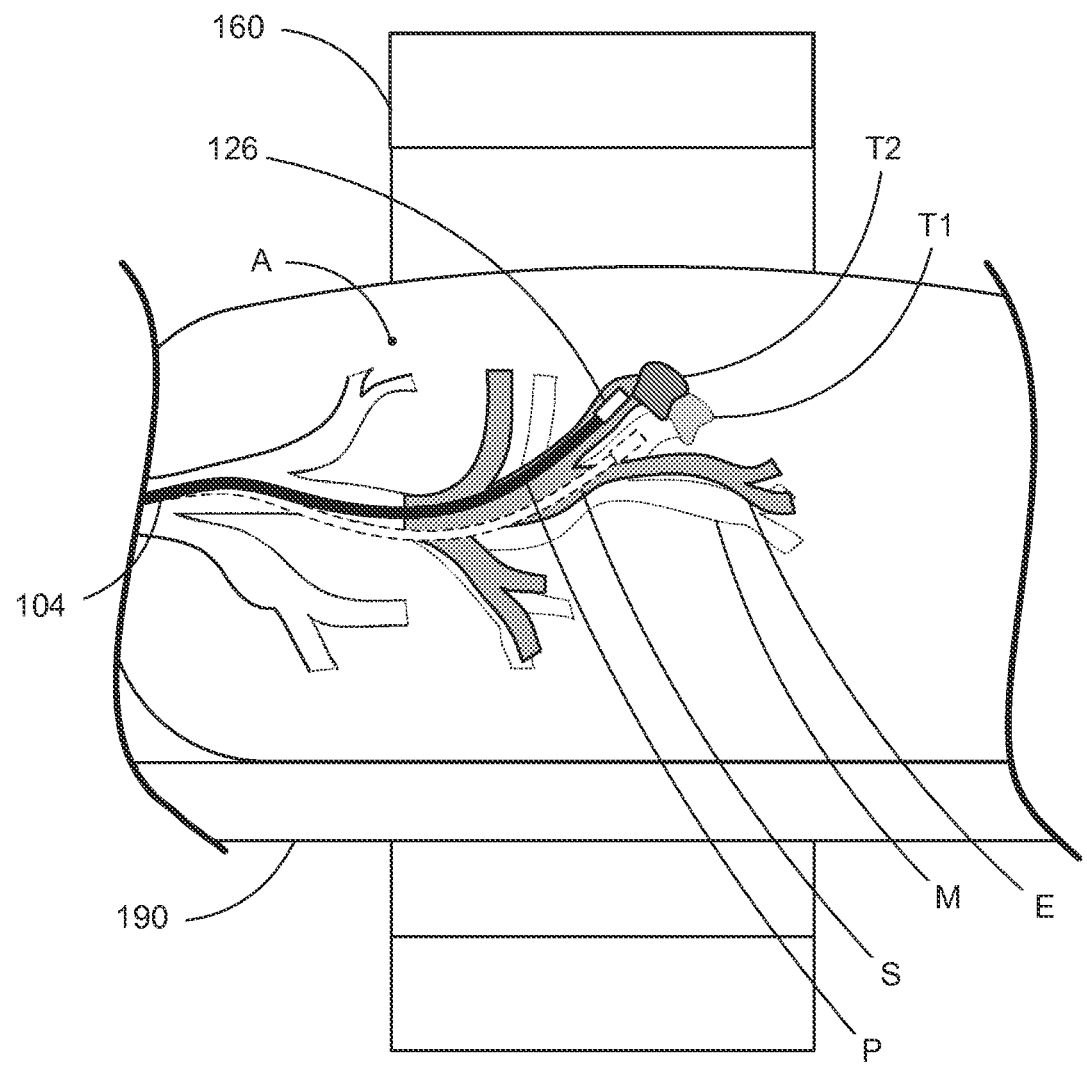

For example, FIG. 2D shows external image data E generated by imaging system 150 (e.g., by the scanning operation described with respect to FIG. 2C) for at least a portion of anatomy A overlaid onto an existing model M of anatomy A for comparative purposes. Note that existing model M can be the original (pre-operative) model of anatomy A, or a modified/updated model generated intraoperatively. Note further that while external image data E is depicted and described herein as a portion or subset of model M of anatomy A, in various other embodiments, external image data E can be the complete anatomy A, although as noted above, scanning only a localized portion of anatomy A can provide beneficial effects (e.g., reduced radiation exposure, increased scan speed, and/or enhanced scan precision, among others). In addition, while external image data E is shown overlaid onto model M for exemplary and descriptive purposes, in various other embodiments, only external image data E or only a modified version of model M (i.e., based on external image data E) could be displayed.

As indicated in FIG. 2D, external image data E further indicates a difference between the actual instrument pose P and the sensor-based instrument pose S (i.e., the pose of the instrument derived from sensor data). Note that while both anatomy-model state and instrument-sensor pose disparities are depicted in FIG. 2D for exemplary purposes, in various embodiments either one or both types of disparities may be present (or significant) in the external image data.

In any event, in various embodiments, any difference between the external image data and measured/modeled states can be used to update the intraoperative modeling and beneficially enhance procedural accuracy (e.g., refine the registration between the anatomical model and the patient anatomy, the instrument, and/or the instrument camera view, adjust/maintain the pose of the instrument, and/or establish a trajectory for the instrument). This can be particularly beneficial when anatomy A is likely to be deformed by the presence and/or movement of instrument 104 (e.g., within the airway tree of the lungs or within an arterial network), and/or the pose of instrument 104 is difficult to accurately establish from sensor or kinematic data (e.g., a flexible instrument).

For example, modeling and registration updates in response to this instrument-caused deformation can be implemented based on instrument sensor data, such as described in co-owned, co-pending patent application Ser. No. 13/893,008. However, in many instances, such sensor-based updates may not precisely represent the actual anatomical condition and/or relative instrument position. In such circumstances, external image data E can be used to refine the intraoperative anatomical model M, improve the registration between instrument 104 and anatomy A, and/or more accurately characterize the relationship between the distal end of instrument 104 and surgical target T2. For example, in response to a modeling or registration discrepancy indicated by external image data E (such as depicted in FIG. 2D), model M, model M itself, the pose of instrument 104, and/or the registration between instrument 104 and model M can be updated to more closely match external image data E.

In some embodiments, the quality and/or accuracy of model M can be enhanced based on external image data E. For example, at a fundamental level, the original model generation (e.g., by pre-operative CT scan segmentation) may not fully capture the anatomy of interest. In such instances, extraneous and/or missing anatomical structures from the original model M can be removed and/or added, respectively, based on the anatomic data extracted form external image data E. For example, the preoperative imaging and segmentation of a branching anatomy such as the airway tree of the lungs may not fully model the smaller elements (branches) of that anatomy, resulting in missing elements. The intraoperative external imaging can in such instances be used to more fully complete the anatomical model, by, for example, identifying and adding missing lumens to the branching anatomy.

In many instances, shape data from shape sensors provide an indication of instrument pose and anatomic state, such as described in U.S. Pat. No. 7,720,322, U.S. patent application Ser. No. 12/839,642, and U.S. patent application Ser. No. 13/107,562, all of which are herein incorporated by reference. In other examples, anatomic and/or instrument shape data extracted from intraoperatively generated external image data E (e.g., via segmentation, feature extraction, or any other processing technique) could be used in conjunction with shape sensor data from instrument 104 to generate accurate 3D models or representations of anatomy A and/or instrument 104 (e.g., via averaging, filtering, or any other algorithms).

In various other embodiments, some or all of the anatomical structures modeled in model M can be identified in external image data E (e.g., using feature extraction techniques such as edge detection, corner detection, shape matching, curve evolution, or any other method), and then used to update the corresponding structures in model M (e.g., by making model M more closely match the extracted image data). In other embodiments, identifiable fiducial elements in, on, or around the patient anatomy and/or instrument can be extracted from external image data E to provide a common registration reference for the model and external image data.

In various other embodiments, the external image data E can be used to identify or confirm the current intraoperative relationship between instrument 104 and anatomy A, optionally in conjunction with updates to model M and/or sensor-based pose S. For example, when tracking the progress of a flexible instrument through a branching anatomy (e.g., a bronchoscope through the airway tree or a catheter through an arterial network), the inherent limits in sensor precision can cause jumpiness or jitter in the pose data. To provide a clearer, more stable graphical user interface (GUI) for such systems, a "snapping" algorithm can be used to display a virtual depiction of the instrument in the closest anatomical passageway, based on the instrument sensor data and the model of the anatomy. However, due to the aforementioned sensor precision limits, anatomical modeling inaccuracies, and/or registration errors, this sort of snapped display may place the instrument in the wrong anatomical passageway.

Therefore, in some embodiments, the intraoperative external image data E can be used to increase the reliability of the snapping algorithm, either by using the extracted anatomical image data and/or instrument image data to refine the anatomical model and/or the instrument pose to enable adjustment of the measured and modeled placement of the instrument within the anatomy, or by extracting the instrument placement data within the anatomy from the external image data, thereby providing a snapshot of the actual placement of the instrument within the anatomy.

This processing of external image data E could be performed by control system 116, external image controller 170, and/or any other processing unit. In other embodiments, the pose of instrument 104 and/or the state of anatomy A could be extracted from external image data E using such feature extraction techniques, and such extracted information could be used by control system 116 to update model M, the pose of instrument 104, and/or the registration of instrument 104 to model M.

In various other embodiments, the external image data can be used to simply provide enhanced direct procedural monitoring and/or performance control. In some embodiments, the external image data can show intraoperative progress and/or activity of a radiopaque (or otherwise visualizable by external imager 160) diagnostic or therapeutic tool or substance (e.g., a therapeutic agent, implantable device, or fiducial) incorporated into or delivered by instrument 104.

Figure 2E:
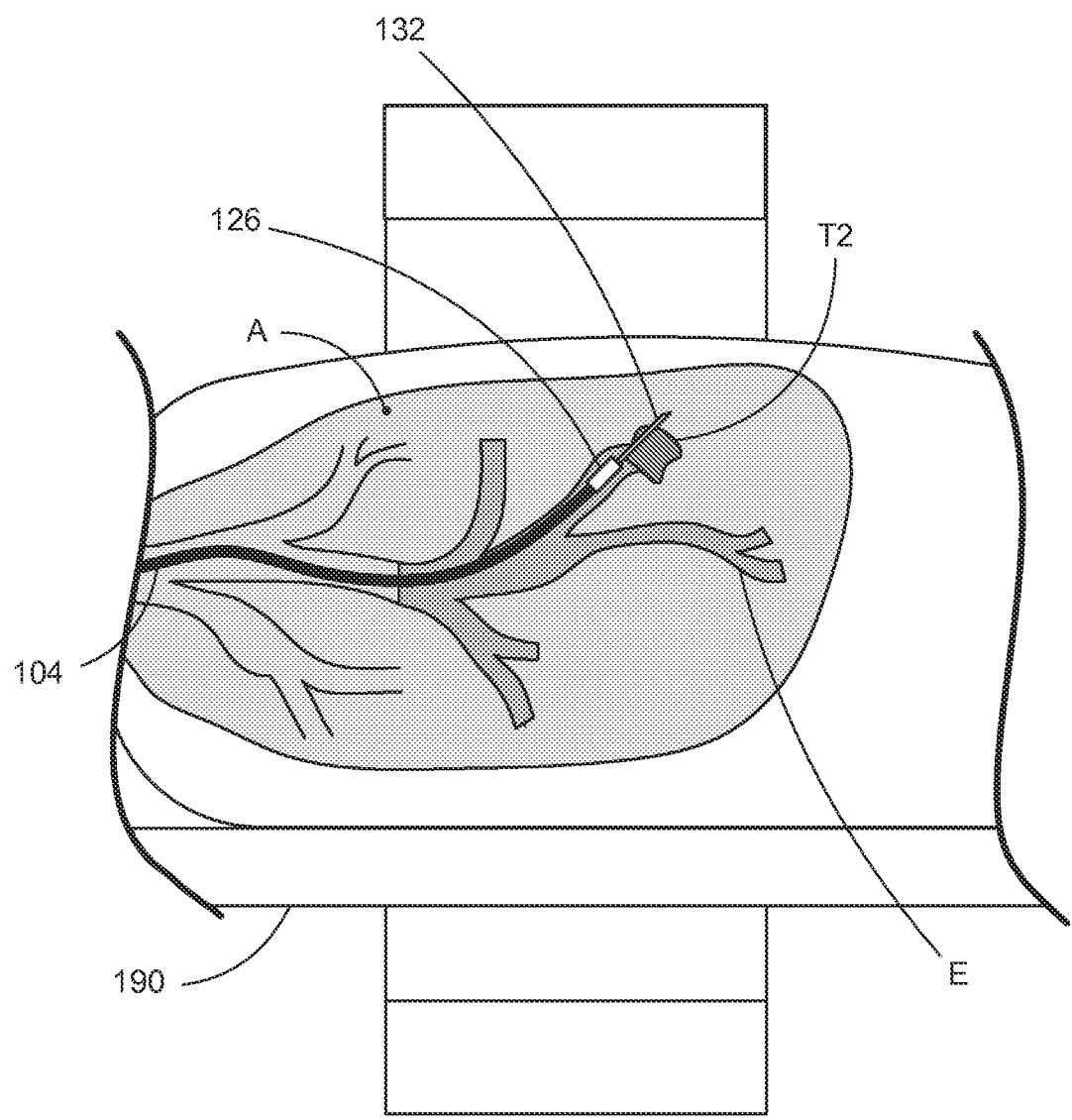

For example, in FIG. 2E, external image data E shows the trajectory of an exemplary tool 132 (e.g., a biopsy, aspiration, or hypodermic needle) through treatment target T2. The instrument pose could be adjusted to optimize procedure performance based on the feature data extracted from external image data E (e.g., relative position information for instrument 104 (and/or distal end region 126 and/or tool 132), anatomy A, and target T2 could be extracted from external image data E, and then used to adjust the pose of instrument 104 to properly align and position tool 132 with respect to target T2). In this manner, the intraoperative delivery of external image data E can minimize the chance that tool 132 is misaligned with target T2.

In other embodiments, the external imaging data could provide confirmation that target T2 is actually being affected by tool 132, thereby ensuring appropriate procedure completion (e.g., confirmation of tissue sampling from, or substance delivery to, target T2). The confirmation could be purely visual (e.g., concurrent display of tool 132 and target T2), or could be an at least semi-automated confirmation (e.g., the image data related to at least one of tool 132 and target T2 are identified via feature extraction or other analysis of external image data E to determine overlap indicating contact between the two).

Figure 2F:
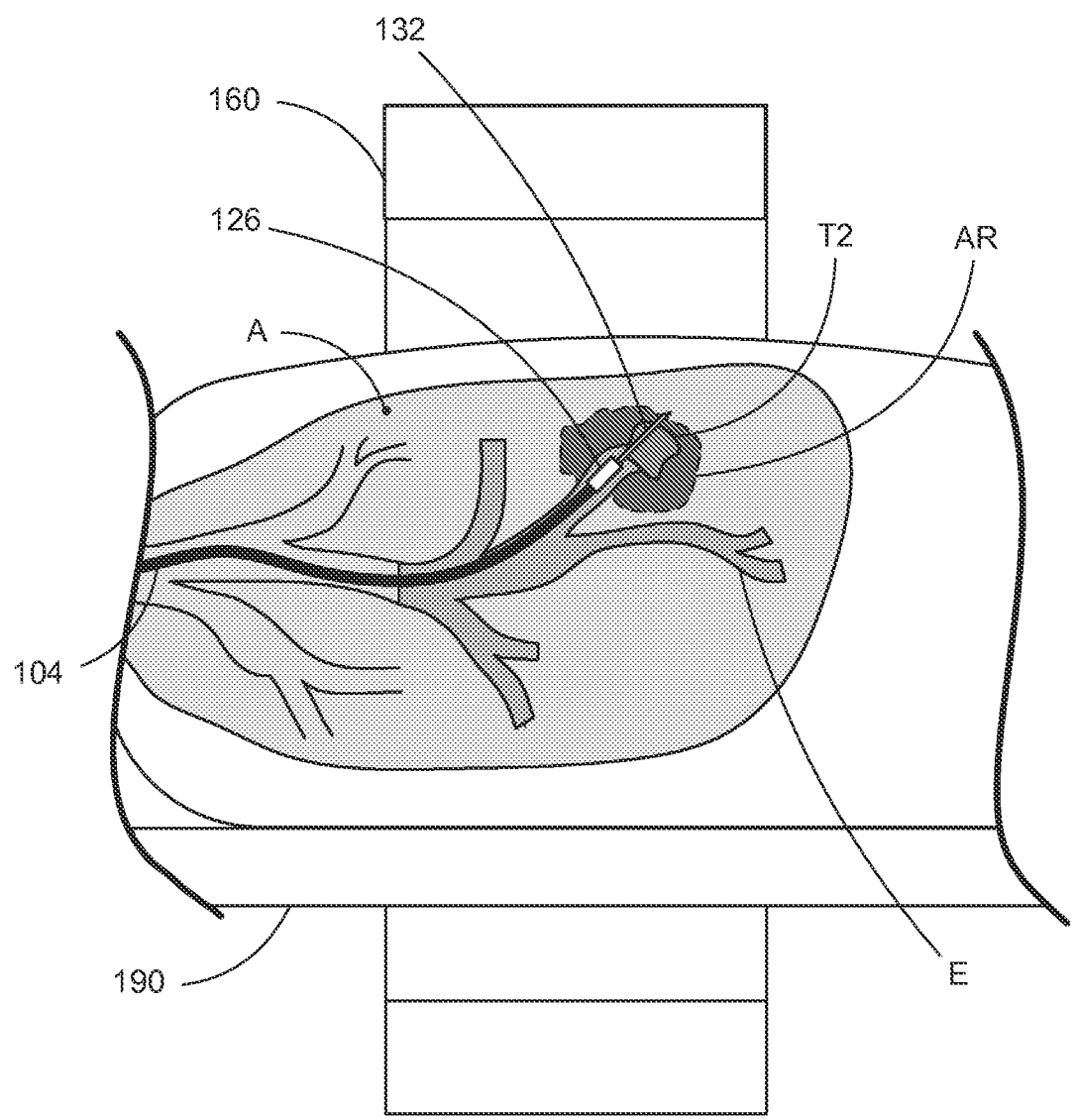

In various other embodiments, the progress and activity of a procedure can be monitored. For example, as shown in FIG. 2F, an affected region AR created by the operation of instrument 104 is detectable by external imager 160 (e.g., via changes in temperature, material distribution/composition, cellular modification, and/or density) and indicated in external image data E.

In some embodiments, affected region AR could indicate the quantity, activity, dispersion, configuration, and/or other behavior of a therapeutic agent (e.g., medicament or cytotoxin), diagnostic agent, anesthetic agent, biologic agent, imaging agent (e.g., indocyanine green (ICG), contrast, or a radiotracer), treatment agent (e.g., radioactive seed implants or radiation-activated nanoparticles), implant (e.g., structural support, functional mechanism, or time-release capsule), fiducial, or any other substance delivered by instrument 104. The size, shape, location, intensity, orientation, or any other characteristic of affected region AR could then be the basis for adjusting a parameter of the substance delivery application (e.g., continuing delivery, increasing/decreasing delivery rate, stopping delivery, adjusting the position/orientation, or changing the content of the substance).

For example, by monitoring affected region AR generated by the delivery of a cytotoxin to target T2, total cytotoxin dosage can be minimized by stopping delivery when affected region AR in external image data E begins to expand beyond target T2. This delivery termination could be user-directed in response to monitoring of affected region AR (e.g., a clinician manually terminates delivery in response to observed state of affected region AR), or could be at least semi-automated (e.g., notification provided or delivery terminated when feature extraction or other algorithm determines that region AR exceeds the boundary of target T2 (either partially or fully) by a predetermined amount).

In various other embodiments, affected region AR could indicate tissue changes in the target region due to temperature increases, radiation dosage, density changes, or any other effect of the applied treatment modality. Similar to the substance delivery monitoring approach described above, the size, location, intensity, or any other characteristic of affected region AR could be the basis for adjusting a parameter of the treatment modality (e.g., adjusting delivery rate, power/intensity, mode of operation, or even simply continuing or stopping the therapy).

For example, by monitoring affected region AR generated by increasing temperature during an ablation procedure, collateral tissue damage can be minimized by terminating ablation when a sufficient portion of target T2 reaches a desired temperature. Similar to the above, this termination of therapy can be user-directed in response to monitoring of affected region AR (e.g., a clinician manually terminates therapy in response to observed state of affected region AR), or could be at least semi-automated (e.g., notification provided or therapy terminated when feature extraction or other algorithm determines that region AR reaches a maximum size, intensity, and/or distribution pattern).

Figure 3A:
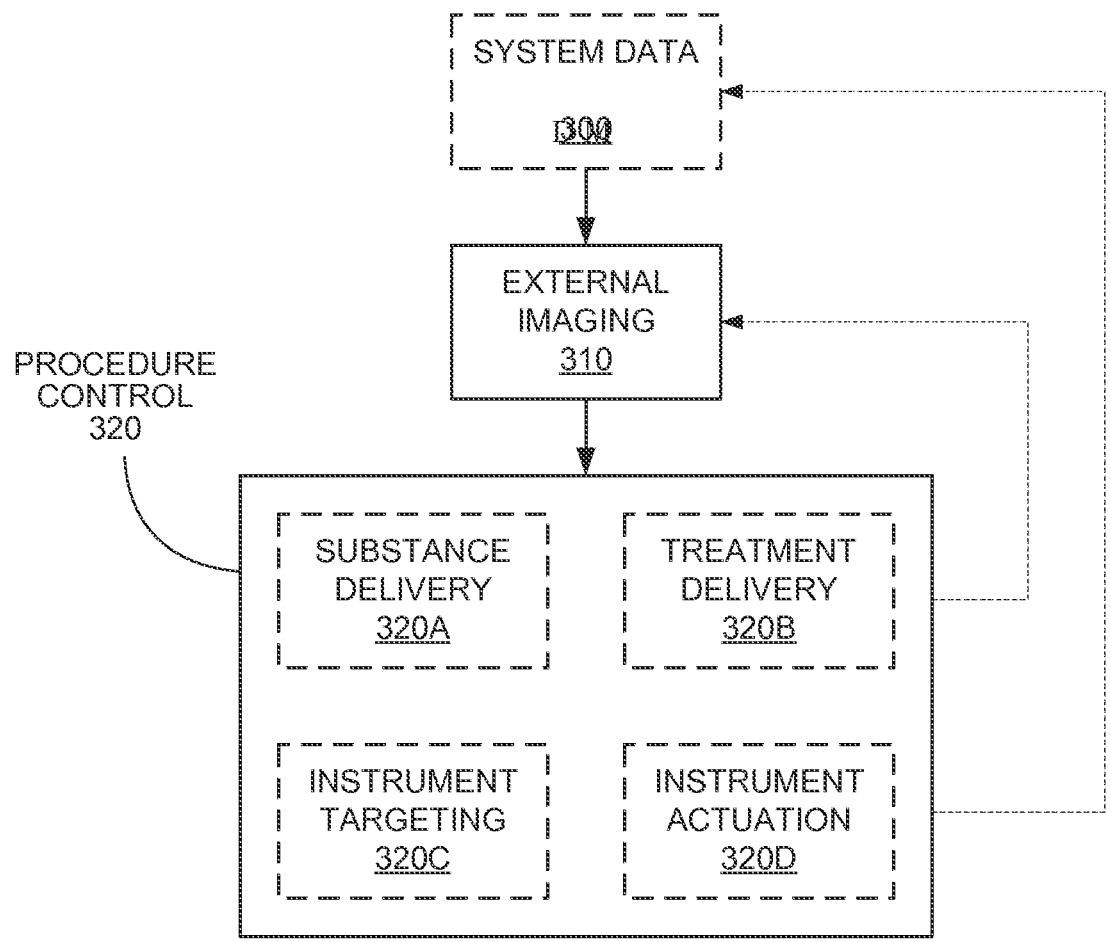
FIGS. 3A-3D show flow diagrams for various procedural approaches involving the use of a robotic medical system in conjunction with external imaging, such as shown in FIGS. 2A-2F.

FIG. 3A shows an exemplary flow diagram for the use of external imaging in a surgical robotic procedure. In an optional SYSTEM DATA GENERATION step 300, an intraoperative model of a patient anatomy and in-use surgical instrument is provided, either based on pre-operative modeling data or intraoperative modeling data, such as described with respect to FIG. 2A above. An external imaging system is then used to intraoperatively generate image data for at least a portion of the patient anatomy in an EXTERNAL IMAGING step 310, such as described with respect to FIG. 2C above. In some embodiments, the imaging of step 310 is performed on the complete anatomical region used to generate the initial model provided in step 300. In various other embodiments, the imaging of step 310 is performed on just a portion of the anatomical region originally modeled.

Figure 3B:
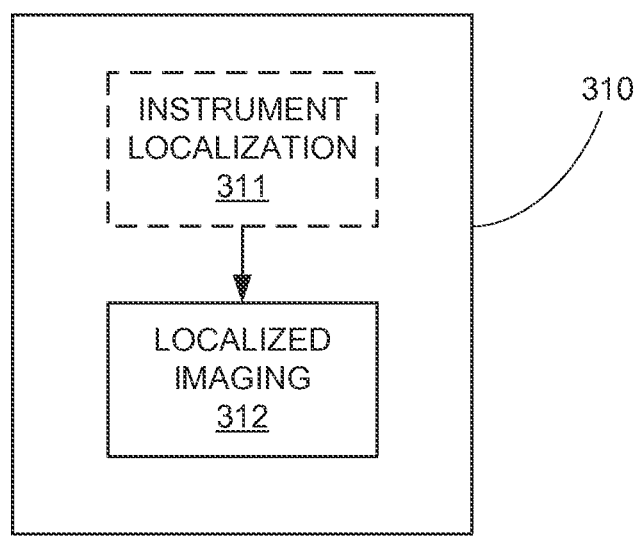

For example, as indicated in the exemplary embodiment of FIG. 3B, step 310 can include a LOCALIZED IMAGING step 312 in which only a portion of the originally modeled anatomy can be imaged, such as described above with respect to FIGS. 2B and 2C. The localized imaging can in some instances beneficially reduce radiation exposure or scan time, and/or enable more detailed imaging of a desired region. In some embodiments, in an optional INSTRUMENT LOCALIZATION step 311, the pose (e.g., position and/or orientation) of the surgical instrument is used as a reference for defining the portion of the anatomy to be imaged in step 312, such as described above with respect to FIG. 2B. In other embodiments, the actual patient anatomy (e.g., an anatomical feature or desired procedure target) can be used as a reference for defining the region imaged in step 312.

Returning to FIG. 3A, the external image data generated in step 310 can then be used to intraoperatively direct the surgical procedure being performed in a PROCEDURE CONTROL step 320. This procedure control can involve any aspect of a given procedure that could benefit from the intraoperative external image data generated in step 310. For example, in some embodiments, step 320 can include an optional SUBSTANCE DELIVERY step 320A, in which a substance (e.g., treatment, diagnostic, or imaging agent, implant, fiducial, or other element) is delivered to a target location. As described above with respect to FIG. 2F, the image data from step 310 could then be used to monitor and/or regulate the substance delivery performed in step 320A.

In various other embodiments, step 320 can include an optional TREATMENT DELIVERY step 320B, in which a treatment (e.g., ablation, radiation, electroporation, etc.) is applied to a target location. As described above with respect to FIG. 2F, the image data from step 310 could then be used to monitor and/or regulate the application of treatment modality in step 320B.

In various other embodiments, step 320 can include an optional INSTRUMENT TARGETING step 320C, in which an instrument (e.g., instrument 104 or any other diagnostic, surgical, or therapeutic instrument) is positioned/oriented with respect to the patient anatomy and/or target surgical location. As described above with respect to FIG. 2E, the pose of an instrument relative to the patient anatomy (e.g., overall anatomic structure or specific target location) can be adjusted based on the intraoperative external image data to enhance procedure outcome.

In various other embodiments, step 320 can include an optional INSTRUMENT ACTUATION step 320D, in which in which an instrument (e.g., instrument 104 or any other diagnostic, surgical, or therapeutic instrument) is actuated (e.g., tissue sampling, resection, dissection, sealing, or suturing, among others), with external image data taken during this instrument actuation to confirm successful performance. As described above with respect to FIG. 2E, the interaction between the instrument and the target anatomy can be detected to confirm procedure outcome. Note that optional steps 320A-320D can be used individually or in any combination. Further, various other optional control operations for step 320 will be readily apparent, including graphical display of any/all of the control effects described above.

Figure 3C:
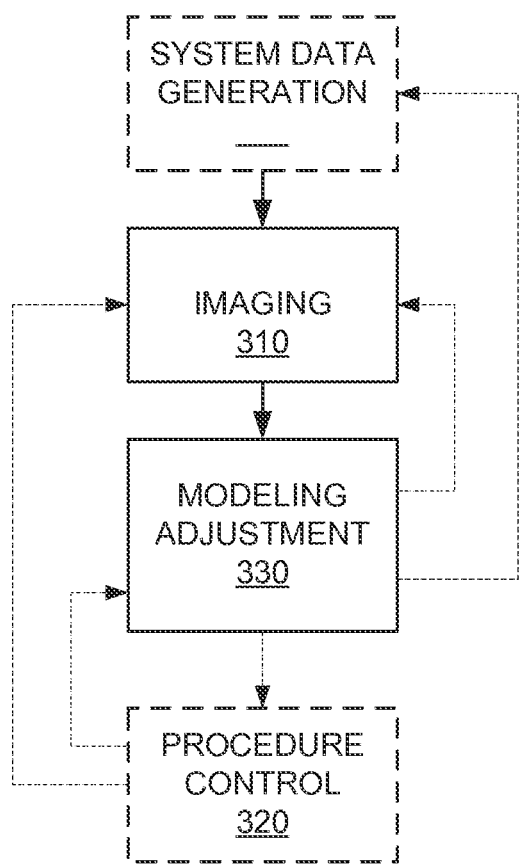

In some embodiments, the external image data can be used to enhance and/or refine the model(s) used in operation and control of the medical robotic system. For example, FIG. 3C shows another exemplary flow diagram for the use of external imaging in a surgical robotic procedure. In an optional SYSTEM DATA GENERATION step 300, an intraoperative model of a patient anatomy and in-use surgical instrument is provided, either based in pre-operative modeling data or intraoperative modeling data, such as described with respect to FIG. 2A above. An external imaging system is then used to intraoperatively generate image data for at least a portion of the patient anatomy in an EXTERNAL IMAGING step 310, such as described with respect to FIG. 2C above. In some embodiments, the imaging of step 310 is performed on the complete anatomical region used to generate the initial model provided in step 300. In various other embodiments, the imaging of step 310 is performed on just a portion of the anatomical region originally modeled (e.g., as described with respect to FIG. 3B).

Figure 3D:
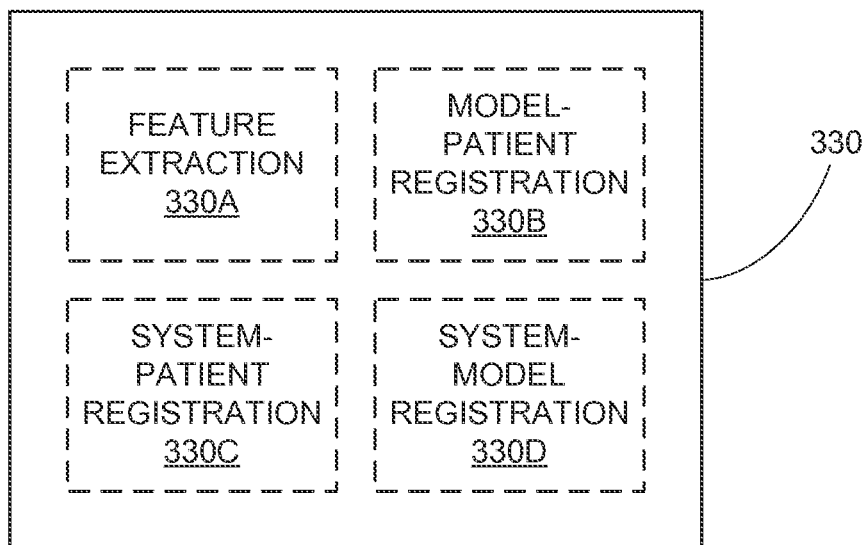

Then, in a MODELING ADJUSTMENT step 330, an update to the modeled anatomy/system is generated and/or applied. The modeling adjustment of step 330 can be any guidance for or modification to the modeling environment used during the procedure being performed. For example, in some embodiments, as shown in FIG. 3D, step 330 can simply be an optional FEATURE EXTRACTION step 330A in which features of interest for the procedure (e.g., anatomical structures, surgical targets, instruments, fiducials, etc.) are identified within the external image data. As noted above, this identification of step 330A can be performed using any number of feature extraction techniques, such as edge detection, corner detection, shape matching, and/or curve evolution, among others.

This extracted feature data can then be used, for example, to update/refine the model provided in step 300, such as described above with respect to FIG. 2D. For example, extracted anatomic feature data from the external image data can be used to update the anatomical model to more accurately represent the intraoperative state of the anatomy and/or update the sensor-based model of the instrument configuration to more accurately represent the intraoperative pose of the instrument.

However, in various other embodiments, the feature data extracted from the external image data can be used to more accurately register the various modeling elements of the procedure environment. In other words, the intraoperative external image data can be used to refine/establish the relationship(s) between the medical robotic system, the patient anatomy, and/or the model of the patient anatomy.

In some embodiments, step 330 can include an optional MODEL-PATIENT REGISTRATION step 330B in which the anatomical model of the patient anatomy is registered more closely to the actual patient anatomy. For example, fiducial data corresponding to fiducial elements (e.g., pads, coils, markings, anatomic structures, or any other elements visible by external imager 160) having a known position and/or orientation relative to the patient anatomy can be extracted from the external image data as described above. The image fiducial data can then provide a reference frame for the image data corresponding to the patient anatomy of interest, thereby allowing the model of the patient anatomy to be properly registered to the actual patient anatomy. For example, by registering the anatomical model of an internal patient anatomical structure (e.g., airway tree) with an external reference fiducial(s), guidance can be provided, or potential issues can be identified, with respect to instrument sizing, procedure path, or any other aspect that could be affected by the (e.g., to provide guidance as to instrument sizing, procedure path planning optimization, or any other aspect of the procedure that could be affected by the internal anatomical state of the patient.

In other embodiments, step 330 can include an optional SYSTEM-PATIENT REGISTRATION step 330C in which the medical robotic system and/or the instrument(s) of that system is registered more closely to the actual patient anatomy. For example, fiducial data corresponding to fiducial elements having a known position and/or orientation relative to the patient anatomy and the medical robotic system/instrument(s) can be extracted from the external image data as described above. The image fiducial data can then establish or refine a common reference frame for system/instrument(s) and the patient anatomy of interest, thereby allowing the system to operate more precisely with respect to the patient anatomy. For example, by registering an instrument to the patient anatomy, an initial incision into the patient that would typically be performed manually (e.g., for the insertion of a cannula for a robotic instrument) could be performed by the medical robotic system without, or with reduced, manual intervention.

In other embodiments, step 330 can include an optional SYSTEM-MODEL REGISTRATION step 330D in which the medical robotic system and/or the instrument(s) of that system is registered more closely to the model of the patient anatomy. For example, fiducial data corresponding to fiducial elements having a known position and/or orientation relative to the patient anatomy and the medical robotic system/instrument(s) can be extracted from the external image data as described above. The image fiducial data can then establish or refine a common reference frame for system/instrument(s) and the anatomic model, thereby allowing the system to be operated more effectively when direct or external visualization is not available. For example, by accurately registering an instrument to the anatomic model, the movement of that instrument within the patient anatomy can be accurately characterized, controlled, and/or monitored, simply via sensors associated with the instrument (e.g., shape sensors, EM sensors, etc.).

Note that optional steps 330A-330D can be used individually or in any combination. Further, various other optional modeling adjustments for step 320 will be readily apparent. In addition, in various other embodiments, the modeling adjustment(s) of step 320 can be used in conjunction with any/all of the procedure control operations of step 320, as indicated in FIG. 3C, and various feedback and adjustment loops are possible among steps 300-330, as indicated by the dashed lines.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method, comprising:
   receiving, from a sensor system coupled to a medical instrument of a medical system, intraoperative pose data for a portion of the medical instrument;
   defining a scan region at least around the portion of the medical instrument, wherein the scan region is defined based on the intraoperative pose data for the portion of the medical instrument, and wherein the scan region includes a subregion of a patient anatomy;
   localizing an imaging area for an intraoperative external imaging system to the scan region;
   receiving, from the intraoperative external imaging system, intraoperative external image data for the subregion of the patient anatomy within the scan region;
   at least semi-automatically controlling the medical system based on the intraoperative external image data to at least adjust a pose of a portion of the medical system based on a first portion of the intraoperative external image data, the first portion of the intraoperative external image data representing a portion of the medical system in the patient anatomy.

2. The method of claim 1, wherein receiving the intraoperative external image data comprises receiving at least one of computerized tomography (CT) scan data, magnetic resonance imaging (MRI) data, positron emission tomography (PET) scan data, fluoroscopic images, thermography data, ultrasonic data, optical coherence tomography (OCT) data, thermal imaging data, impedance imaging data, laser imaging data, or nanotube X-ray imaging data.

3. The method of claim 1, wherein the subregion of the patient anatomy is only within a predetermined region around a distal end region of the medical instrument.

4. The method of claim 1, wherein the intraoperative external image data includes image data for a target location in the patient anatomy, and wherein at least semi-automatically controlling the medical system further comprises delivering a substance to the target location using the medical system.

5. The method of claim 4, wherein at least semi-automatically controlling the medical system further comprises displaying the intraoperative external image data to depict the substance at the target location.

6. The method of claim 4, wherein at least semi-automatically controlling the medical system further comprises:
   identifying image data for the substance in the intraoperative external image data; and
   adjusting a control parameter for delivering the substance based on the image data for the substance.

7. The method of claim 4, wherein the substance comprises at least one of a therapeutic agent, a diagnostic agent, anesthetic agent, treatment agent, or an imaging agent.

8. The method of claim 4, wherein the substance comprises at least one of an implant, a fiducial, or a time release capsule.

9. The method of claim 1, wherein the intraoperative external image data includes image data for a target location in the patient anatomy, and wherein at least semi-automatically controlling the medical system further comprises applying a treatment modality using the medical system to the target location in the patient anatomy.

10. The method of claim 9, wherein at least semi-automatically controlling the medical system further comprises displaying the intraoperative external image data to show an effect of the treatment modality at the target location.

11. The method of claim 9, wherein at least semi-automatically controlling the medical system further comprises:
    identifying an effect of the treatment modality in the intraoperative external image data; and
    adjusting a parameter of the treatment modality based on the effect of the treatment modality identified in the intraoperative external image data.

12. The method of claim 9, wherein the treatment modality comprises at least one of ablation, radiation, or ultrasound.

13. The method of claim 1, wherein at least semi-automatically controlling the medical system further comprises:
    identifying the first portion of the intraoperative external image data representing the portion of the medical system in the patient anatomy.

14. The method of claim 13, wherein at least semi-automatically controlling the medical system further comprises identifying a second portion of the intraoperative external image data representing a target anatomical region, and wherein adjusting the pose of the portion of the medical system is further based on the second portion of the intraoperative external image data.

15. The method of claim 1, wherein the medical system comprises a focal therapy system, and wherein at least semi-automatically controlling the medical system comprises:
    identifying a target portion of the intraoperative external image data representing a procedure target in the patient anatomy; and
    adjusting a parameter of the focal therapy system based on the target portion.

16. The method of claim 15, wherein the focal therapy system comprises an external beam radiotherapy instrument for generating a radiation beam, and wherein adjusting the parameter of the focal therapy system comprises:

determining a target shape from the target portion; and defining a beam shape for the radiation beam based on the target shape.

17. The method of claim 1, wherein the medical system comprises the medical instrument, and wherein at least semi-automatically controlling the medical system comprises displaying the intraoperative external image data to show at least one actuation state of the medical instrument.

18. The method of claim 17, wherein the medical instrument comprises at least one of a forceps, rongeur, scalpel, biopsy tool, suturing tool, stapler, or vessel sealer.

19. The method of claim 1, wherein the intraoperative external image data includes shape data corresponding to a shape of the medical instrument of the medical system within the patient anatomy.

20. The method of claim 19, wherein at least semi-automatically controlling the medical system comprises adjusting a pose of the medical instrument based on the intraoperative external image data.

* * * * *